US00PP31294P3

(12) United States Plant Patent
Larse

(10) Patent No.: US PP31,294 P3
(45) Date of Patent: Dec. 31, 2019

(54) STRAWBERRY PLANT NAMED 'ALICIA'

(50) Latin Name: ***Fragaria* x *ananassa***
Varietal Denomination: Alicia (a.k.a. '109180')

(71) Applicant: SWEET DARLING SALES, INC., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 15/932,838

(22) Filed: May 4, 2018

(65) Prior Publication Data

US 2018/0324992 P1 Nov. 8, 2018

Related U.S. Application Data

(60) Provisional application No. 62/501,253, filed on May 4, 2017.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

(56) References Cited

PUBLICATIONS https://www.alamy.com/stock-photo-strawberry-fragaria-alice-growing-in-a-clay-terracotta-pot-80317457.html; Jun. 29, 2012; 1 page*
GTITM UPOVROM Citation For 'Alice' as per QZ PBR 20000098; Apr. 14, 2000; 1 page.*

* cited by examiner

*Primary Examiner* — Kent L Bell
(74) *Attorney, Agent, or Firm* — Cooley LLP

(57) ABSTRACT

The present invention provides new and distinct strawberry plant designated as 'Alicia' (a.k.a. '109180').

6 Drawing Sheets

Latin name of the genus and species: *Fragaria* x *ananassa.*

Varietal denomination: 'Alicia' (a.k.a. '109180').

BACKGROUND OF THE INVENTION

The present invention relates to new and distinct strawberry plant designated as 'Alicia' (a.k.a. '109180').

'Alicia' (a.k.a. '109180') is the result of a controlled-cross made on May 29, 2013 between a female parent cultivar designated 105218 (a.k.a., 'Zaralina') and a male parent cultivar designated 102850 (a.k.a., 'Victor') made by the Inventor and was first fruited in Watsonville, Calif. growing fields. Following selection and during testing, the plant was originally designated '109180' and subsequently named 'Alicia'. 'Alicia' is a day-neutral plant.

This new strawberry plant was asexually reproduced via runners (stolons) by the inventor at Watsonville, Calif. Asexual propagules from the original source have been tested in Watsonville growing fields and to a limited extent, grower fields in high elevation. The properties of this plant were found to be transmissible by such asexual reproduction. The plant is stable and reproduces true to type in successive generations of asexual reproduction.

BRIEF SUMMARY OF THE INVENTION

This invention relates to new and distinctive strawberry plant designated as 'Alicia' (a.k.a. '109180'). The plant is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

'Alicia' has not been observed under all possible environmental conditions, and the phenotype may vary significantly with variations in environment, however with no variance in genotype. The following observations, measurements, and comparisons describe this plant as grown under normal conditions in Watsonville, Calif. unless otherwise noted.

The following traits and photographs in combination distinguish strawberry plant 'Alicia' from known strawberry plants. Plants for the botanical measurements in the present application were grown as annuals. Any color references are made to The Royal Horticultural Society Colour Chart, 1995 Edition, except where general terms of ordinary dictionary significance are used. The plants were 8-month old when the observation was made.

TABLE 1

'Alicia' Characteristics

| | Characteristic | Description |
|---|---|---|
| General | Plant Habit | Perennial |
| | Plant Growth Habit | Upright |
| | Day Length | Day Neutral |

TABLE 1-continued

'Alicia' Characteristics

| | Characteristic | Description |
|---|---|---|
| | Height (cm) | 34 |
| | Width (cm) | 35 |
| | Density of foliage | low |
| | Plant vigor | moderate |
| | Crown Diameter | 4 cm |
| | Fertility | Self-fertile |
| | Freezing quality | moderate |
| Leaf | Leaf shape | Concave |
| | Leaf variegation | Absent |
| | Leaflets per leaf | 3 |
| | Number of leaflets | 88 to 128 |
| | Terminal leaflet width (mm) | 93 |
| | Terminal leaflet length (mm) | 86 |
| | Terminal leaflet length/width ratio | 1.08 |
| | No. teeth/terminal leaflet | 24 |
| | Shape of terminal leaflet | Orbicular |
| | Shape of the terminal leaflet apex | Rounded |
| | Shape of the terminal leaflet base | acute |
| | Shape of terminal leaflet in cross-section | concave |
| | Margin description of the terminal | serrate to crenate |
| | Color of upper side of leaves | RHS 137A |
| | Color of lower side of leaves | RHS 139C |
| | Terminal leaflet margin | revolute |
| | Leaf blistering | weak |
| | Leaf glossiness | medium |
| | Petiole length (cm) | 20 |
| | Petiole diameter (mm) | 4.8 |
| | Petiole color | RHS 145A |
| Limbs | Petiolule length (cm) | 0.95 |
| | Petiolule diameter (mm) | 3.83 |
| | Petiolule color | RHS 145B |
| | Stipule length (cm) | 4 |
| | Stipule width (cm) | 1.4 |
| | Stipule pubescence | sparse |
| | Stipule anthocyanin | Present |
| | Stipule color (color code) | RHS 145C |
| | Stipule anthocyanin color | RHS 185B |
| | Pedicel color (color code) | 145A |
| | Attitude of hairs on petiole and pedicel | upwards |
| | Inflorescence position relative to foliage | above |
| | flower arrangement of petals | free |
| | Petal length (cm) | 1 |
| | Peduncle length | 16 cm |
| | Peduncle diameter | 4.54 mm |
| | Peduncle color (color code) | RHS 145A |
| | Peduncle pubescence | Medium to dense |
| | Attitude of hairs on peduncle and pedicel | upwards |
| Inflorescence | Inflorescence position relative to foliage | Above |
| | Number of Flowers | 22 to 38 |
| | Flower arrangement of petals | free |
| | Petal length | 1.0 |
| | Petal width (cm) | 1.1 |
| | Petal length/width ratio | 0.91 |
| | Petal number per flower | 5 to 6 |
| | Upper Petal color | RHS 155C |
| | Lower Petal color | RHS 155D |
| | Petal shape | Orbicular |
| | Petal apex | rounded |
| | Petal base shape | concave |
| | peduncle size | medium |
| | Calyx diameter (cm) | 3.7 |
| | Calyx diameter relative to corolla | larger |
| | Inner calyx diameter relative to outer calyx | Smaller to equal |
| | Sepal number per flower | 10 to 14 |
| | Sepal length (cm) | 1.3 |
| | Sepal width (cm) | 0.5 |

TABLE 1-continued

'Alicia' Characteristics

| | Characteristic | Description |
|---|---|---|
| | Sepal shape | Elliptical |
| | Sepal apex | Convex |
| | Sepal margin | Entire |
| | Corolla diameter (cm) | 2.6 |
| | Sepal length (cm) | 1.3 |
| | Sepal width (cm) | 0.5 |
| | Time of flowering (50% of plants in bloom) | March |
| | Shape of stigma | capitate |
| | Color of stigma | RHS 172A |
| | Length of style (mm) | 1.12 |
| | Color of style | RHS 6A |
| | Color of the ovary | RHS 145B |
| | Receptacle color | RHS 145A |
| | Length of the stamens (mm) | 4.6 |
| | Anther diameter (mm) | 0.8 |
| | Anther length (mm) | 1.2 |
| | Number of stamen | 26 |
| | Shape of anther | dorsifixed |
| | Size of anther | medium |
| | Color of anther | RHS 12A |
| | Amount of pollen | moderate to high |
| | Color of pollen | RHS 22A |
| | Color of filament | RHS 149D |
| | Length of filament (mm) | 2.73 |
| | Number of flowers per truss | 3 to 6 |
| Stolon | Stolon number | 3 to 11 |
| | Stolon anthocyanin | RHS 181A |
| | Widest diameter of stolon At leaf attachment (mm) | 3.3 |
| | Stolon color | RHS 145A |
| | Stolon Length | 52.67 cm |
| | Stolon anthocyanin | RHS 181A |
| | Stolon thickness | medium |
| | Stolon pubescence | medium |
| | Widest diameter of stolon at leaf attachment | 3.3 mm |
| Fruit | Number of fruit per truss | 3 to 5 |
| | Fruit length (cm) | 4.7 |
| | Fruit width (cm) | 4.1 |
| | Fruit length/width ratio | 1.15 |
| | Relative fruit size | medium |
| | Fruit calyx diameter (cm) | 5.2 |
| | Fruit skin color | RHS 45A |
| | Fruit flesh color excluding core | RHS 41A |
| | Fruit core color | RHS 49A |
| | Color of calyx | RHS 137C |
| | Position of calyx | Below surface |
| | Level of adherence of calyx | strong |
| | Pose of calyx segments | reflexed |
| | Size of calyx in relation to fruit | Equal to larger |
| | Fruit weight (g) | 28 |
| | Predominant fruit shape | globose conic |
| | Shape difference between primary & secondary fruits | No shape difference |
| | Width of band without of achenes | medium |
| | Fruit glossiness | medium |
| | Position of achenes | even |
| | Achene color | RHS 149A |
| | Achenes per fruit | 308 |
| | Achene weight (g) | 0.22 |
| | Position of achenes in relation to skin surface | even |
| | Surface texture | Smooth |
| | Texture when tasted | medium |
| | Position of calyx | inserted |
| | Level of adherence of calyx | strong |
| | Color of calyx | RHS 137C |
| | Firmness of flesh | firm |
| | Evenness of flesh color | nearly even |
| | Sweetness Brix | 8 |
| | Type of bearing | Day neutral |
| | Time of fruit ripening | May |

TABLE 1-continued

| 'Alicia' Characteristics | |
|---|---|
| Characteristic | Description |
| Harvest maturity (50% of plants with ripe fruit) | June |
| Appearance score (1 to 5 with 5 = best) | 3.5 |
| Storage longevity | 5 to 10 days |
| pH | 3.46 |
| Yield (grams per plant per season) | 2206 |
| Hollow core length (cm) | 1.9 |
| Hollow core width (cm) | 1.1 |
| Hollow core length/width ratio | 1.73 |
| Hollow core size | medium |

'Alicia' is distinguished from its paternal parent by its larger fruit size, greater ease of harvest, and its presentation of shorter and thicker petioles. 'Alicia' is distinguished from its maternal parent by its larger fruit size, greater yield volume, and longer flower stems. 'Alicia' is similar to the variety 'Monterey' (U.S. Plant Pat. No. 19,767), but possesses several distinguishing traits from Monterey. 'Alicia' is distinguished from 'Monterey' by its greater ease of harvest, smaller plant size, and higher berry yield per plant. 'Alicia' presents shorter and thicker petioles than 'Monterey'. 'Alicia' has a lower cull rate than 'Monterey' and both of its parents. 'Albion' (U.S. Plant Pat. No. 16,228) is a commercial strawberry variety that is similar to, but distinguished from 'Alicia'. The fruit yield of 'Alicia' exceeds the yield of 'Albion' in multiple annual testing cycles performed at the breeders test location in Watsonville Calif.

In addition, 'Alicia' scored better than it's parents for percent marketable fruit of the sum of all fruit produced in Watsonville Calif. test plots. Compared to its parents, 'Alicia' was observed to withstand adverse post harvest ambient temperatures over several days, demonstrating a putative longer shelf life as well as less susceptibility to the discoloration effect associated with bruising that occurs during the hand harvesting procedure. The fruit of each of the parents of the strawberry plant variety named 'Alicia' was observed to be lighter in redness coloration 'Alicia'. One parent of 'Alicia', a strawberry plant variety named 'Victor' (a.k.a., 102850), was determined to be a short day variety, whereas 'Alicia' has been determined to be a day neutral type when grown in the breeder's Watsonville Calif. test farm. The color of the foliage of 'Victor' is a lighter green than it's offspring 'Alicia'. 'Victor' produces more fruit over the fruiting season than it's offspring 'Alicia', however 'Alicia' produces fruit during a longer period of time than it's short-day parent 'Victor'. The other parent of 'Alicia', a strawberry plant variety named 'Zaralina' (a.k.a., 105218) produces much less fruit than 'Alicia', and the plant structure of 'Zaralina' is smaller and more compact than 'Alicia'. The strawberry plant variety named 'Alicia' produces more stolon in the fruiting field than either of it's parents when grown in the breeder's Watsonville location.

DESCRIPTION OF THE DRAWINGS

The accompanying color photographs depict various characteristics of the cultivars as nearly true as possible to make color reproductions.

Figure 1:
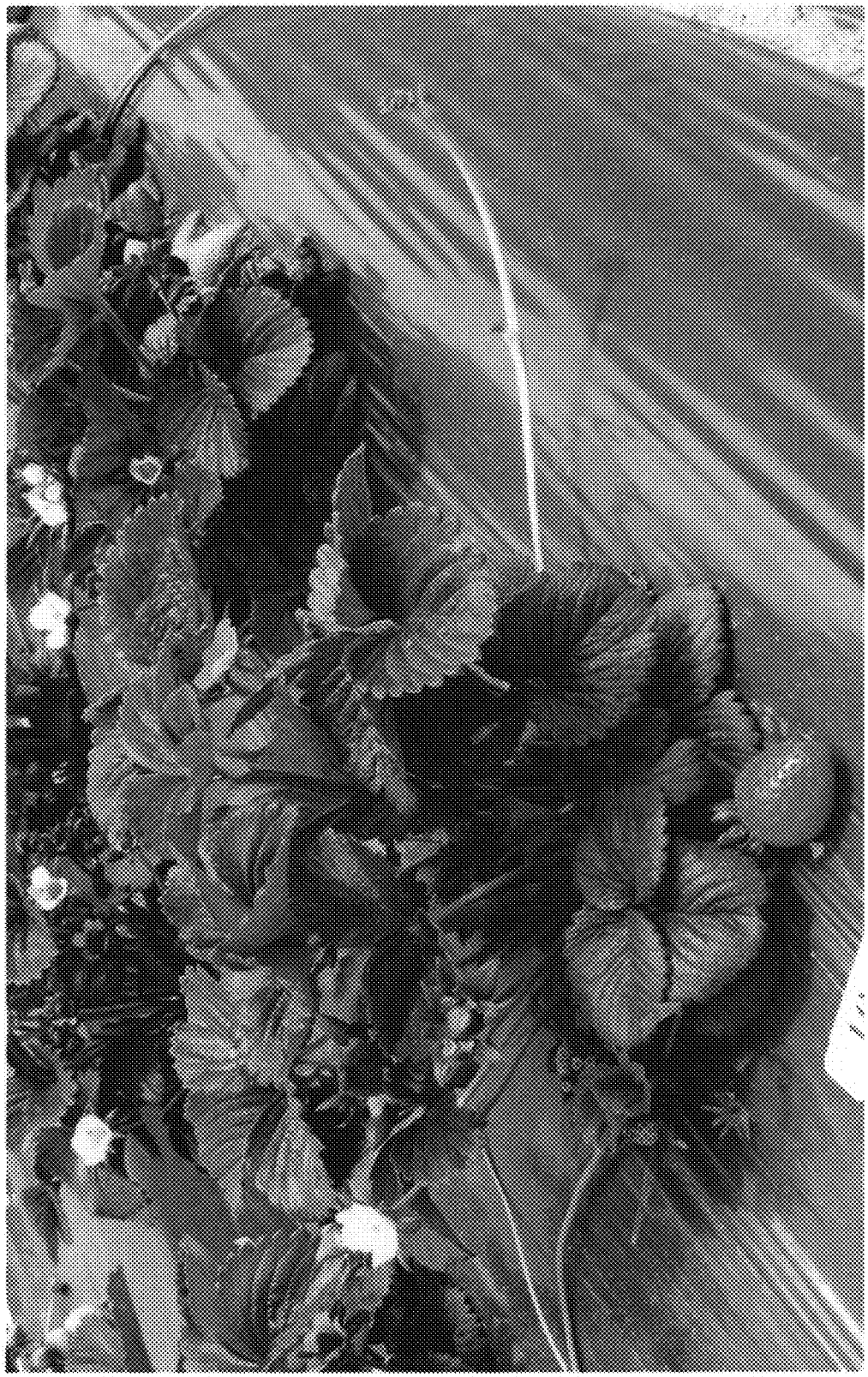
FIG. 1 shows ripe and near-ripe fruits of 'Alicia' about 6-month old.
Figure 2:
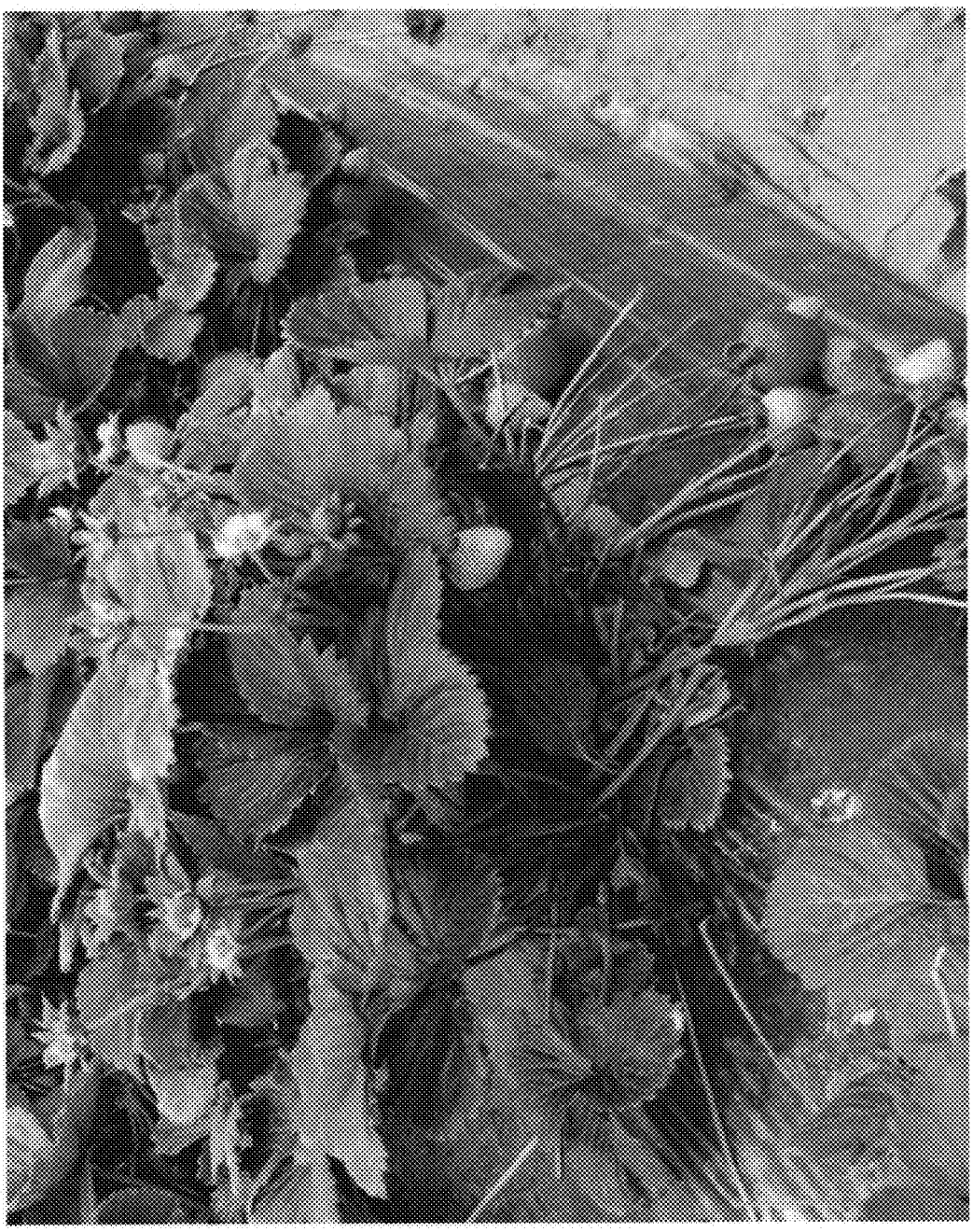
FIG. 2 shows 'Alicia' plants growing in the field with multiple fruits.
Figure 3:
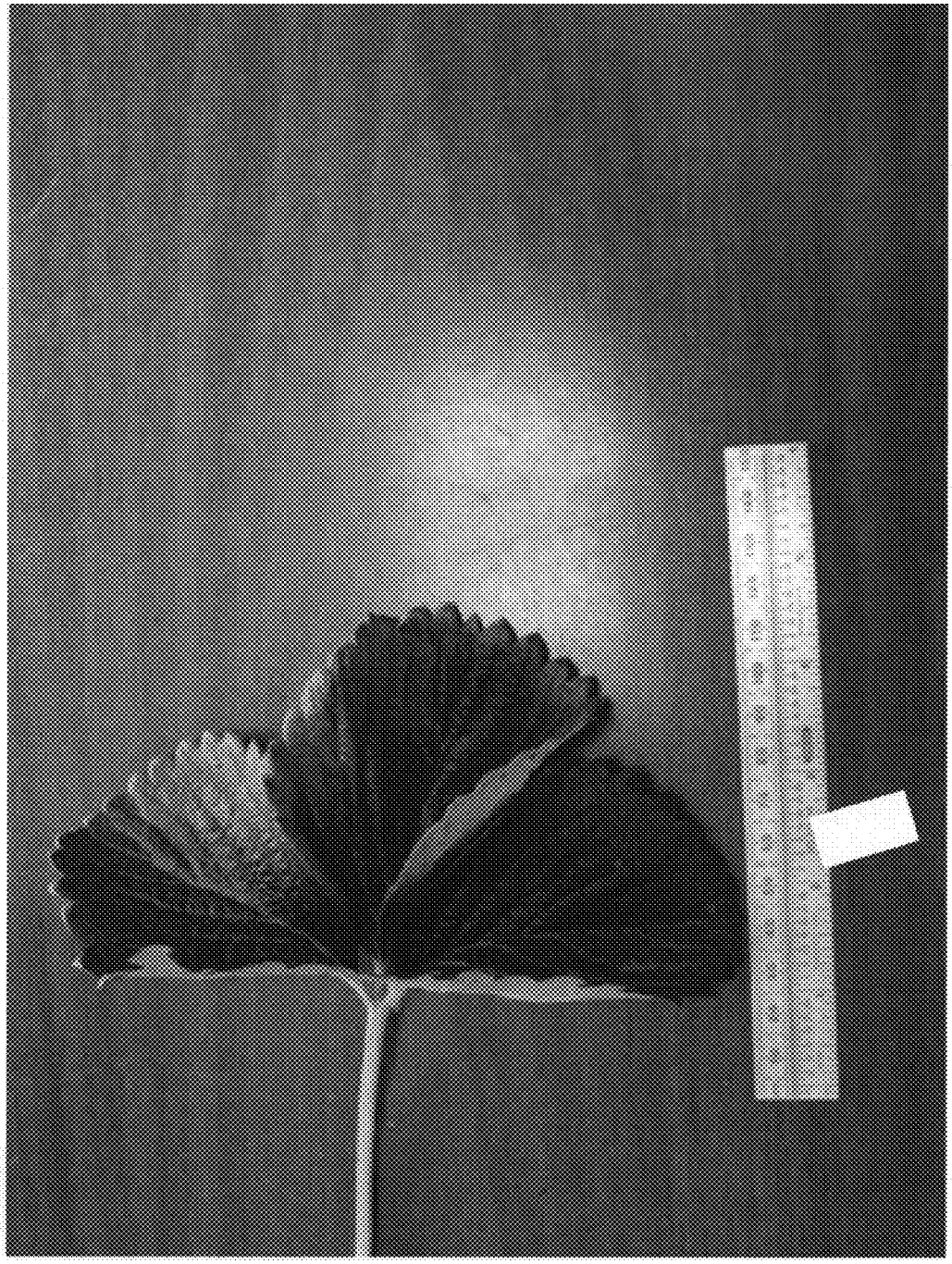
FIG. 3 shows the front side of a leaf of 'Alicia' plants.
Figure 4:
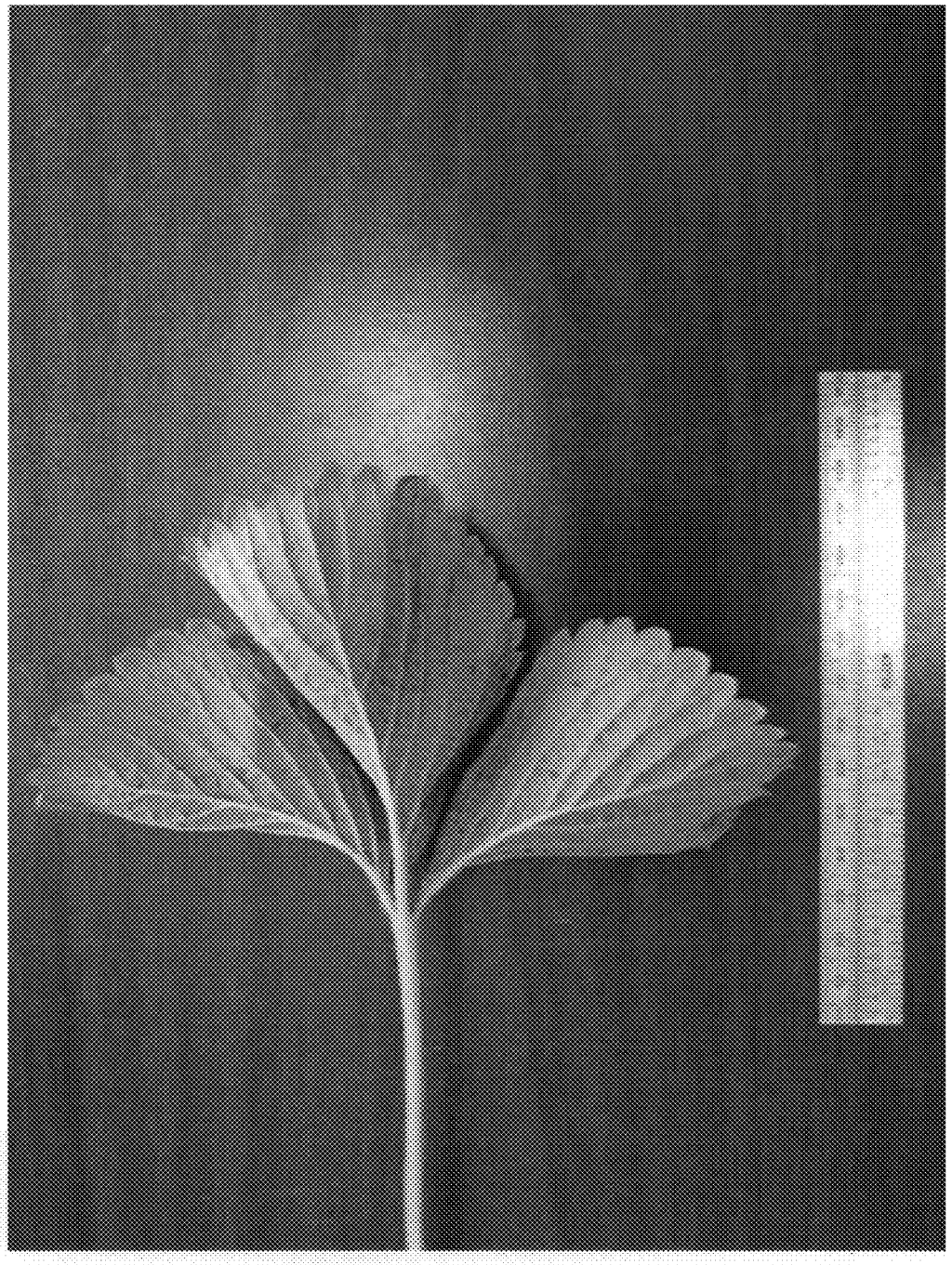
FIG. 4 shows the back side of a leaf of 'Alicia' plants.
Figure 5:
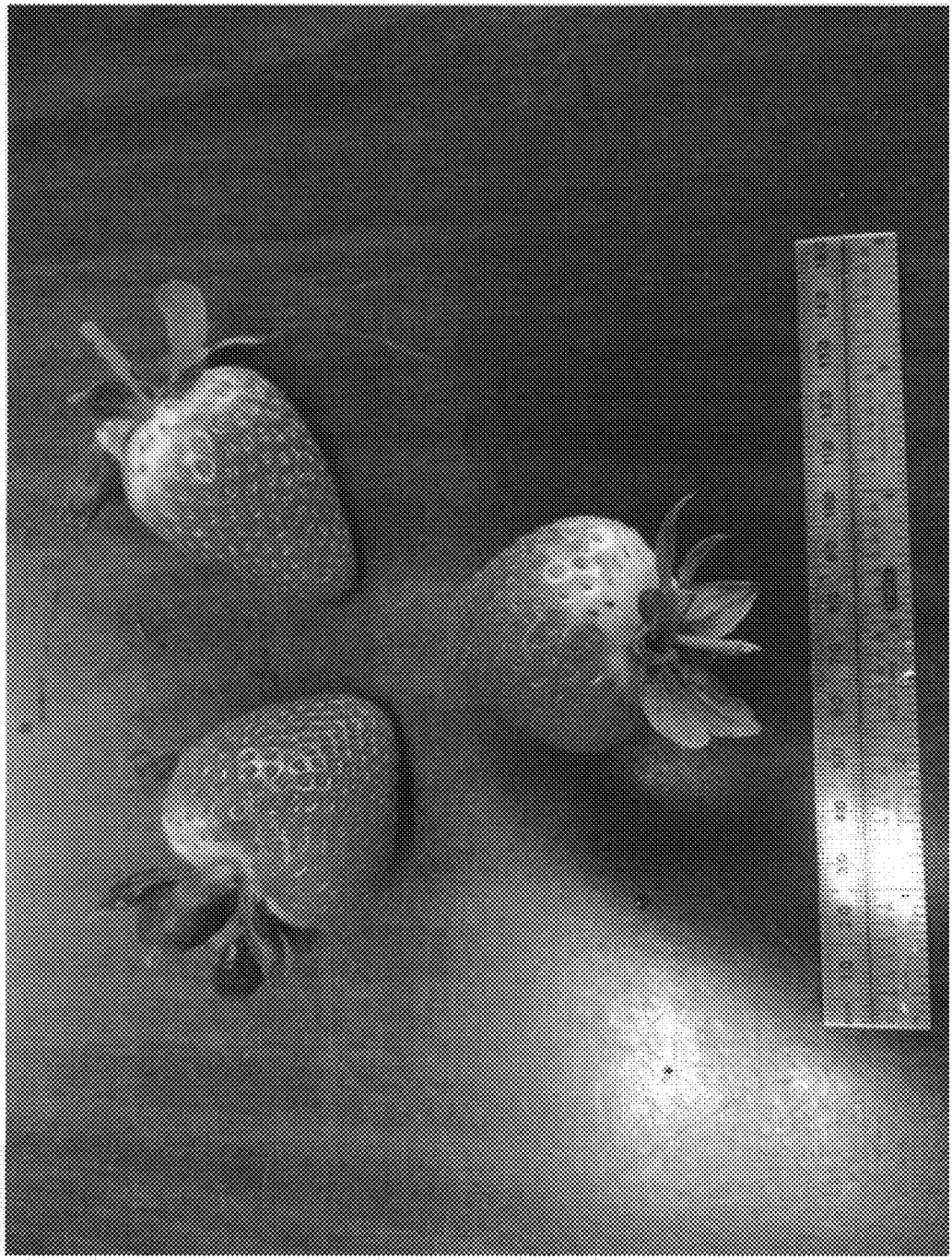
FIG. 5 shows fruits of 'Alicia' plants.
Figure 6:
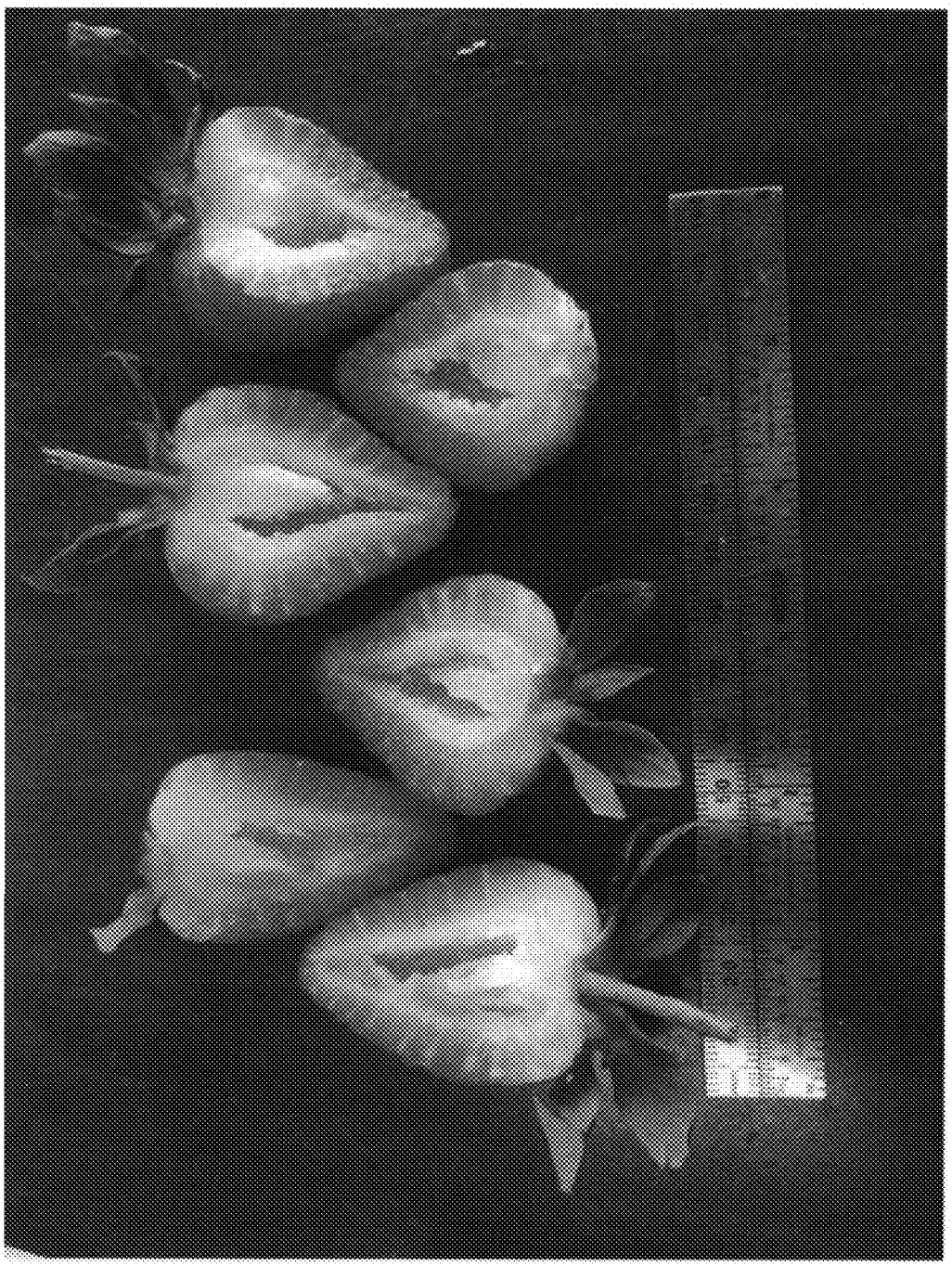
FIG. 6 shows fruits of 'Alicia' plants cut in half.

The invention claimed is:

1. A new and distinct cultivar of strawberry plant named 'Alicia', substantially as shown and described herein.

* * * * *